United States Patent
Reinhardt et al.

[11] Patent Number: 6,059,743
[45] Date of Patent: May 9, 2000

[54] KNEE-JOINT ORTHESIS

[75] Inventors: Holger Reinhardt, Kempen; Rainer Scheuermann, Kiel; Hans Bruno Bauerfeind, Kempen, all of Germany

[73] Assignee: Bauerfeind Orthopadie GmbH & Co., KG, Germany

[21] Appl. No.: 09/077,004

[22] PCT Filed: Sep. 16, 1997

[86] PCT No.: PCT/EP97/05072

§ 371 Date: May 18, 1998

§ 102(e) Date: May 18, 1998

[87] PCT Pub. No.: WO98/14144

PCT Pub. Date: Apr. 9, 1998

[30] Foreign Application Priority Data

Sep. 16, 1996 [DE] Germany .......................... 196 37 728

[51] Int. Cl.[7] .................................................. A61F 5/00
[52] U.S. Cl. .............................................. 602/26; 602/16
[58] Field of Search .................................... 602/5, 16, 20, 602/23, 26, 27, 60–63, 22, 21; 623/39, 47, 48, 59, 27, 28; 482/127; 16/221; 403/52, 53, 54, 83; D24/190

[56] References Cited

U.S. PATENT DOCUMENTS

| | | |
|---|---|---|
| 585,789 | 1/1897 | Kirby ........................................ 602/26 |
| 3,898,709 | 8/1975 | Lewis et al. . |
| 4,353,361 | 10/1982 | Foster ........................................ 602/26 |
| 4,379,463 | 4/1983 | Meier et al. ............................... 602/26 |
| 4,986,264 | 1/1991 | Miller ........................................ 602/16 |
| 5,443,444 | 8/1995 | Pruyssers .................................. 602/26 |
| 5,626,557 | 5/1997 | Mann ........................................ 602/26 |
| 5,658,243 | 8/1997 | Miller et al. ............................... 602/26 |

FOREIGN PATENT DOCUMENTS

| | | |
|---|---|---|
| 32 05 046 | 10/1982 | Germany . |
| 3825813 | 2/1990 | Germany . |
| 42 29 044 | 3/1993 | Germany . |
| 108380 | 3/1925 | Switzerland . |

*Primary Examiner*—Kim M. Lee
*Attorney, Agent, or Firm*—Banner & Witcoff, Ltd.

[57] ABSTRACT

The invention relates to a knee-joint orthesis with fastening means for the thigh and the lower leg, which fastening means are connected to one another via at least one two-part rail comprising a pivot hinge which is offset rearwards in relation to the knee joint, to adapt to the pattern of movement of the latter, and which includes a pin. The pin is mounted eccentrically in a pivot bearing which connects both rail parts in a rotationally movable manner and, by its turning movement, continuously displaces the position of the pin, this displacement into its respectively adapted position being effected by the movement of the knee joint.

3 Claims, 4 Drawing Sheets

KNEE-JOINT ORTHESIS

This application is a national stage application of PCT EP 9705072 filed Sep. 6, 1997.

FIELD OF THE INVENTION

The invention relates to a knee-joint orthesis with fastening means for the thigh and the lower leg, which fastening means are connected to one another via at least one two-part rail comprising a pivot hinge which is offset rearwards in relation to the knee joint, to adapt to the pattern of movement of the latter, and which includes a pin.

BACKGROUND OF THE INVENTION

A knee-joint orthesis of this type is depicted and described in European Patent Application 705,582. The known knee-joint orthesis has, on both sides of the knee to be supported, two-part rails which in each case terminate with their ends in cup-like fastening means with which the orthesis is attached to the thigh and the lower leg. The two parts of each rail are connected via in each case one hinge, with one hinge (of the inner rail) consisting of one pin, and the other hinge (of the outer rail) consisting of two mutually articulated brackets, which cross one another and are in each case hinged with their one end on the one fastening means and with their other end on the other fastening means.

The principle of connecting two-part rails of a knee-joint orthesis so that they are rotationally movable is based on the recognition that the knee joint executes a rolling and sliding movement. This movement is discussed in a publication by A. Bähler "Die biomechanischen Grundlagen der Orthesen-versorgung des Knies" [The biomechanical principles of orthotic fixtures for the knee], Orthopädie-Technik 2/89, pages 52–59. FIG. 6 on page 54 of this publication shows a "compromise pin" as per Nietert, found on the basis of tests discussed in the publication. In this regard, the introduction to the publication states, on page 52, left column, paragraph 1, as follows: The results show that single-pin rails with a 16 mm rearward offset of the pin for medium-sized patients, two-hinge rails with toothing, four-pin hinges and physiological hinges with migrating pin still best satisfy the requirements.

In orthopaedics, a large number of knee-joint ortheses have been proposed which to a greater or lesser extent take account of the above-described findings. Apart from complicated knee-joint ortheses with a multiplicity of bracket and lever connections, which are associated with substantial technical complexity, extensive use is made of ortheses in which their two rail parts are connected only by a single pin. For the optimum configuration of such an orthesis, the position of this pin in relation to the knee joint is crucial. European Patent Specification 393,081 describes a knee-joint orthesis in which on each side of the knee there is in each case a single-pin pivot hinge whose position in relation to two fastening means on the thigh and lower leg is brought about by a displacement of arms attached to the hinges, which arms are provided with a plurality of holes for selective connection to matching pieces attached to the fastening means. By using the holes, the hinges can be advanced to a greater or lesser extent toward the fastening means. This obviously involves a relatively complex mechanism which additionally permits only an incremental adaptation of the position of the pivot hinges to the fastening means.

SUMMARY OF THE INVENTION

The invention is based on the object of making available a knee-joint orthesis according to the features set out in the introduction, which, with a simple structure, permits practically automatic adaptation of the position of its pin on an individual basis to the movement of the knee of the respective patient. According to the invention, this is achieved by the fact that the pin is mounted eccentrically in a pivot bearing which connects both rail parts to one another in a rotationally movable manner and, by its turning movement, continuously displaces the position of the pin, this displacement into its respectively adapted position being effected by the movement of the knee joint.

Depending on the intensity of the treatment of the patient's knee considered necessary, the knee-joint orthesis according to the invention can be provided with only one two-part rail, which is then to be arranged either on the inner side or outer side of the knee, or else the knee-joint orthesis is provided with two two-part rails on both sides of the knee, by which means a particularly stable guidance of the knee to be treated is of course obtained.

On account of the eccentric bearing of the pin in the pivot bearing, which connects the two rail parts to one another in a rotationally moveable manner, a pressure force or tensile force is exerted on the pin when the knee is moved, these forces being transmitted to the pivot bearing and turning the latter relative to the two rail parts in such a way that the pin finally assumes a position in which the pin is largely adapted to the pattern of movement of the knee joint, i.e. ini which the position of the pin largely coincides with the abovementioned "compromise pin". It is of particular advantage in this respect that the displacement of the pin to adapt to the movement of the knee joint takes place along the arc of a circle, because of the eccentric bearing of the pin, so that this movement has both a component transverse to the leg and also a component lengthways to the leg. This affords a particularly good possibility of adaptation of the position of the pin to the respective knee joint movement in the sense of a displacement of the pin as close as possible to the "compromise pin".

This adaptation of the position of the pin is effected by the knee joint movement of the respective patient, who automatically brings about an individual adaptation to his/her particular anatomical features, if appropriate with different displacement of the pin on the right side and left side of the knee-joint orthesis, without this necessitating an intervention in the sense of any sort of manipulation.

Depending on the therapy deemed necessary by the treating physician, it may be a matter of allowing the displacement of the position of the pin with the turning of the pivot bearing to take place continuously upon movement of the knee joint, or, if fixing of the pin is preferred, or locking this pin in its adapted position so that, starting from this locked position, the pin correspondingly guides the knee joint, as a result of which the knee joint is protected against:. incorrect movements.

In order to treat this latter case, the pivot bearing is expediently provided with means for locking it in relation to the rail. When the pin has found its adapted position by means of the knee-joint movement, the pivot bearing is locked by a locking member so that the pin position is thus fixed. With releasable locking means, this fixing can of course once again be cancelled, by which means it is possible, if longer therapy makes it necessary, to again adapt the position of the pin to the possibly altered circumstances of the patient, e.g. as a result of strengthening of his/her musculature through training.

To securely hold the two-part rail in the knee-joint orthesis, the rail is expediently pushed with its two parts in each case into a pocket on the fastening means for the thigh and for the lower leg. In order to ensure that the rail, after it has been introduced into the pockets, can also be removed again, the pockets are expediently designed such that one pocket is closed all along its side and is open toward the pivot hinge, while the other pocket has an opening, extending in its longitudinal direction, for the insertion and removal of the rail, and which is covered by a covering flap which can be closed by means of a touch-and-close fastener.

BRIEF DESCRIPTION OF THE FIGURES

Illustrative embodiments of the invention are represented in the figures, where.

DETAILED DESCRIPTION OF THE INVENTION

Figure 1:
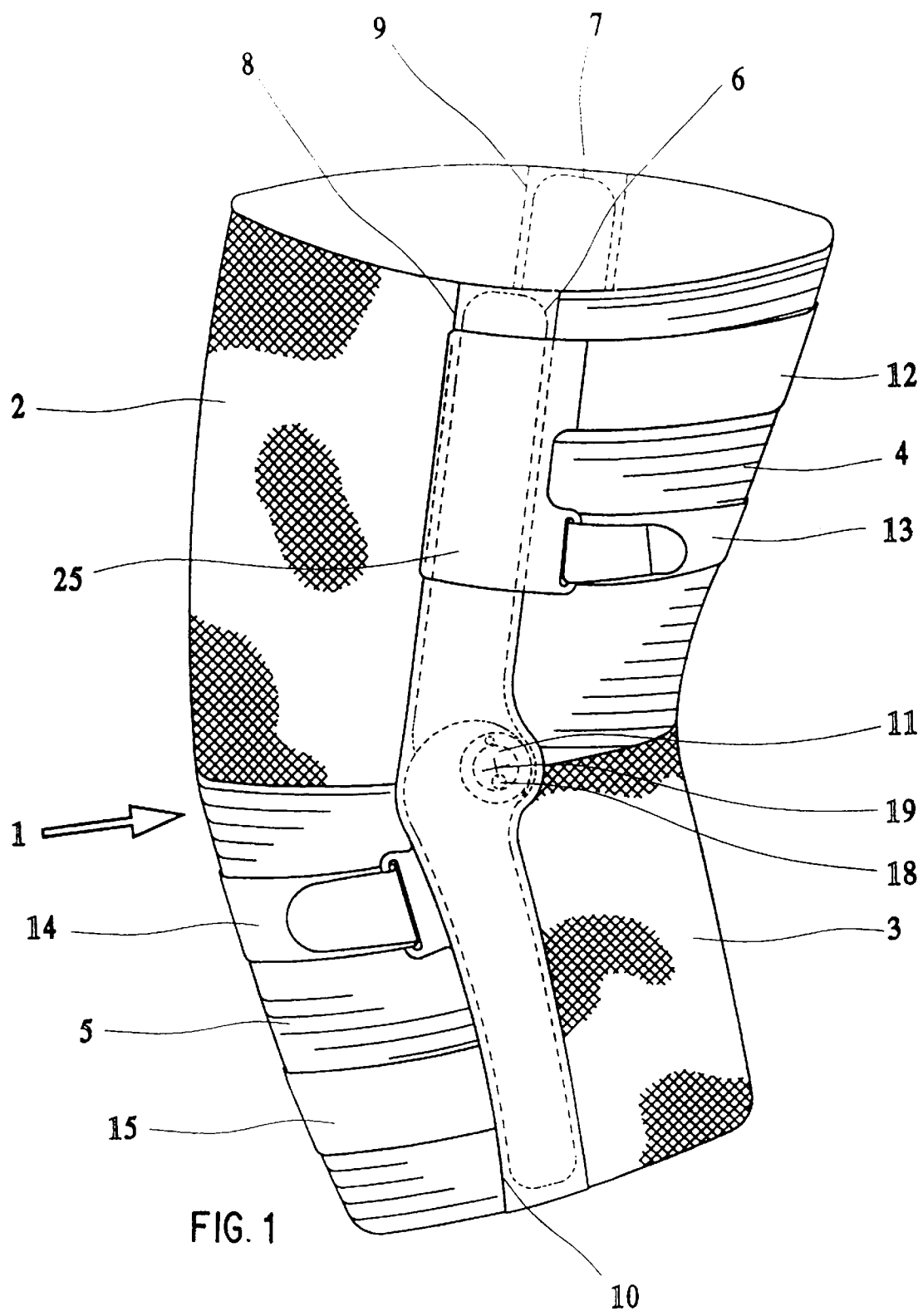
FIG. 1 shows the knee-joint orthesis viewed from the side.

FIG. 1 shows the knee-joint orthesis 1 which is formed by a tube, and the two non-elastic tube parts 2 and 3, and the elastic tube parts 4 and 5. The non-elastic tube parts 2 and 3 are, as it were, arranged diagonally relatively to each other, which is also true of the elastic tube parts 4 and 5. In the area of the junction of the nonelastic tube parts 2/3 and the elastic tube parts 4/5, the two-part rails 6 and 7, which are arranged on both sides of the knee-joint orthesis 1, are indicated. The two parts of each of the two rails 6 and 7 are pushed into pockets 8, 9 and 10 and enclosed tightly by these, so that upon movement of the knee, and thus of the tube parts 2/3 and 4/5, the two parts of each of the rails 6 and 7 turn with respect to one another about the pin 18. As regards the arrangement of the pin 18, reference should be made to the statements concerning FIG. 2. The elastic tube parts 4 and 5 of the knee-joint orthesis 1 are bridged by the non-elastic bands 12, 13, 14 and 15 which are fastened to the non-elastic tube parts 2 and 3 and, after application to a knee, remove the circumferential elasticity from the elastic tube parts 4 and 5, by which means the knee-joint orthesis 1 is made to fit securely on the knee.

Figure 2:
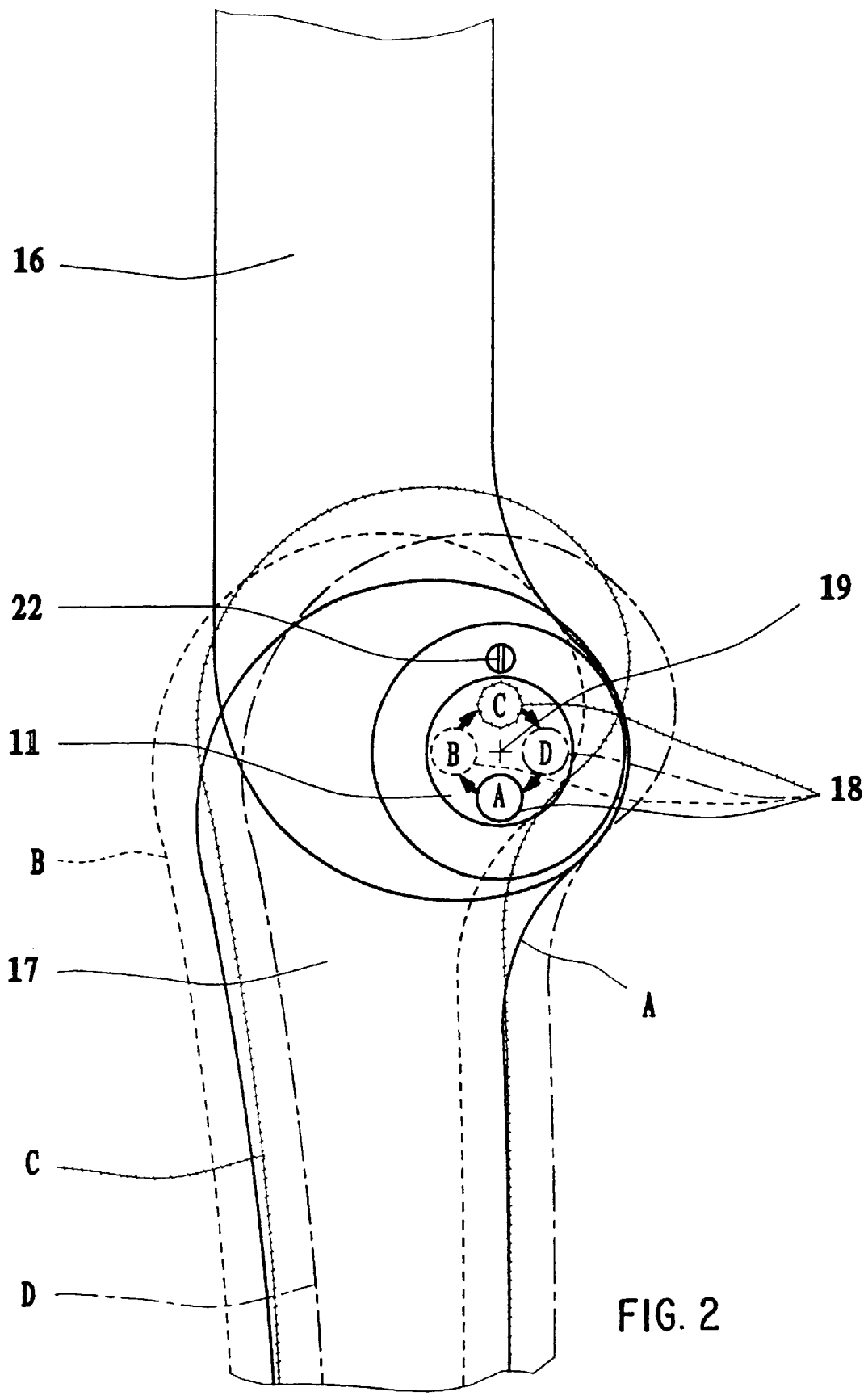
FIG. 2 shows the pivot bearing of a two-part rail of the pivot hinge orthesis according to FIG. 1 on an enlarged scale.

FIG. 2 represents a two-part rail, corresponding to the rail 6 from FIG. 1, with its upper part 16 and its lower part 17. The rail 16/17 contains the pivot bearing 11 via which the upper part: 16 is connected to the lower part 17. The pivot bearing 11 is a disc-like structure which, as can be seen from FIG. 3 discussed below, can be inserted into the upper part 16 such that it can turn. The pivot bearing 11 contains the eccentric pin 18 which additionally penetrates the lower part 17 and thus forms the pivot: axis about which the upper part and lower part can turn with respect to one another. On account of the ability of the pivot bearing 11 to turn, it is possible to move the pin 18 in relation to the upper part 16 on a circular trajectory which is obtained by means of the eccentricity of the pin 18 in relation to the center of the pivot bearing 11. This center is indicated by the broken line 19 in FIG. 3. In FIG. 2, the center of the pivot bearing 11 is represented by the cross 19 marked at its center.

As a result of the pivot bearing 11 turning, the positions indicated in FIG. 2 by the letters A, B, C, D (and continuously all intermediate positions) can be obtained for the pin 18, by which means said pin 18 assumes a corresponding position in each case. This results in the relative position of upper part 16 and lower part 17 which is indicated in FIG. 2 by lines corresponding to the borders of the pin positions A, E, C and D. On the basis of these different lines, it will be seen that, in relation to the respective line, the associated knee-joint orthesis 1 is displaced relative to the pivot bearing 11, which in relation to the knee enclosed by the knee-joint orthesis 1 means that the pin 18 is correspondingly displaced in relation to the enclosed knee. The pin 18 can thus be displaced with the pivot bearing 11, relative to the knee joint concerned, over the range of the circular trajectory containing the pin positions A, B, C, D, by which means a considerable adaptation possibility for approximation to the "compromise pin" is achieved.

Figure 3:
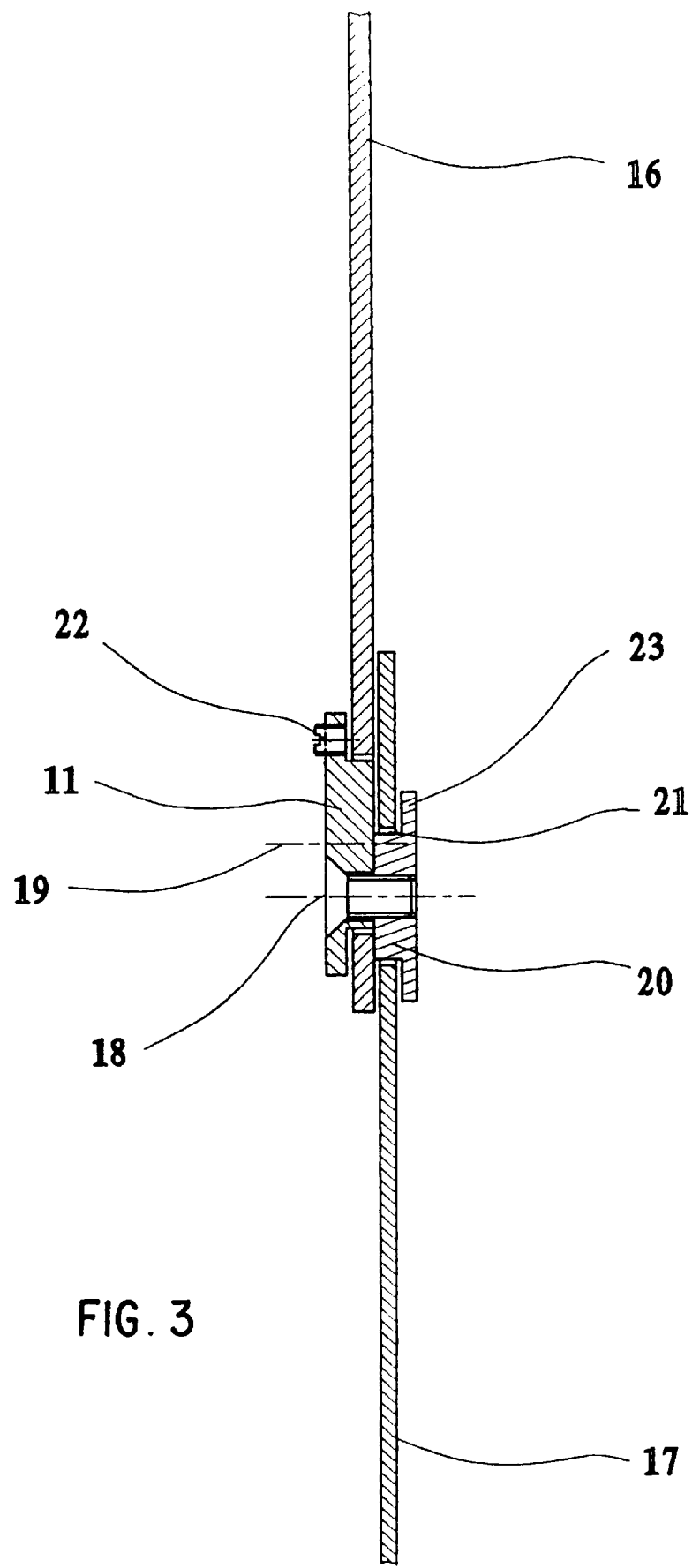
FIG. 3 shows a two-part rail with the pivot bearing in cross section.

From FIG. 3, which shows the rail 16/17 from FIG. 2 in cross section, it will be seen that the pivot bearing 11 is held on the upper part 16 by means of a screw, the latter at the same time forming the pin 18 for the turning of upper part 16 and 17 relative to one another. The screw forming the pin 18 is screwed centrally into the nut 20 which is accommodated in a corresponding drilled hole 21 of the lower part 17 and is held securely on the lower part 17 by means of the flange 23.

As a consequence of the above-described configuration of the pivot bearing 11 with the pin 183 and the nut 20, an eccentric bearing of the pin 18 relative to the center 19 of the pivot bearing 11 is obtained, as is discussed above with reference to the pin positions A, B, C and D. This arrangement means that the pivot bearing 11 can be turned easily in the upper part 16, so that when a knee-joint orthesis 1 is applied to a knee and the knee is moved, the pivot bearing 11 is displaced into a position in which the pin 18 is brought as close as possible to the "compromise pin".

In order to fix the pivot bearing 11 relative to the upper part 16 once the pin 18 has in this way been brought to the most favorable position, a grub screw 22 is provided which, when tightened, presses said pin against the upper part 16 and thereby fixes the pivot bearing 11 relative to the upper part 16. The pin 18 is thus at the same time fixed relative to the upper part 16, as a result of which a non-displaceable pin is provided for the turning of upper part 16 and lower part 17 relative to one another.

Figure 4:
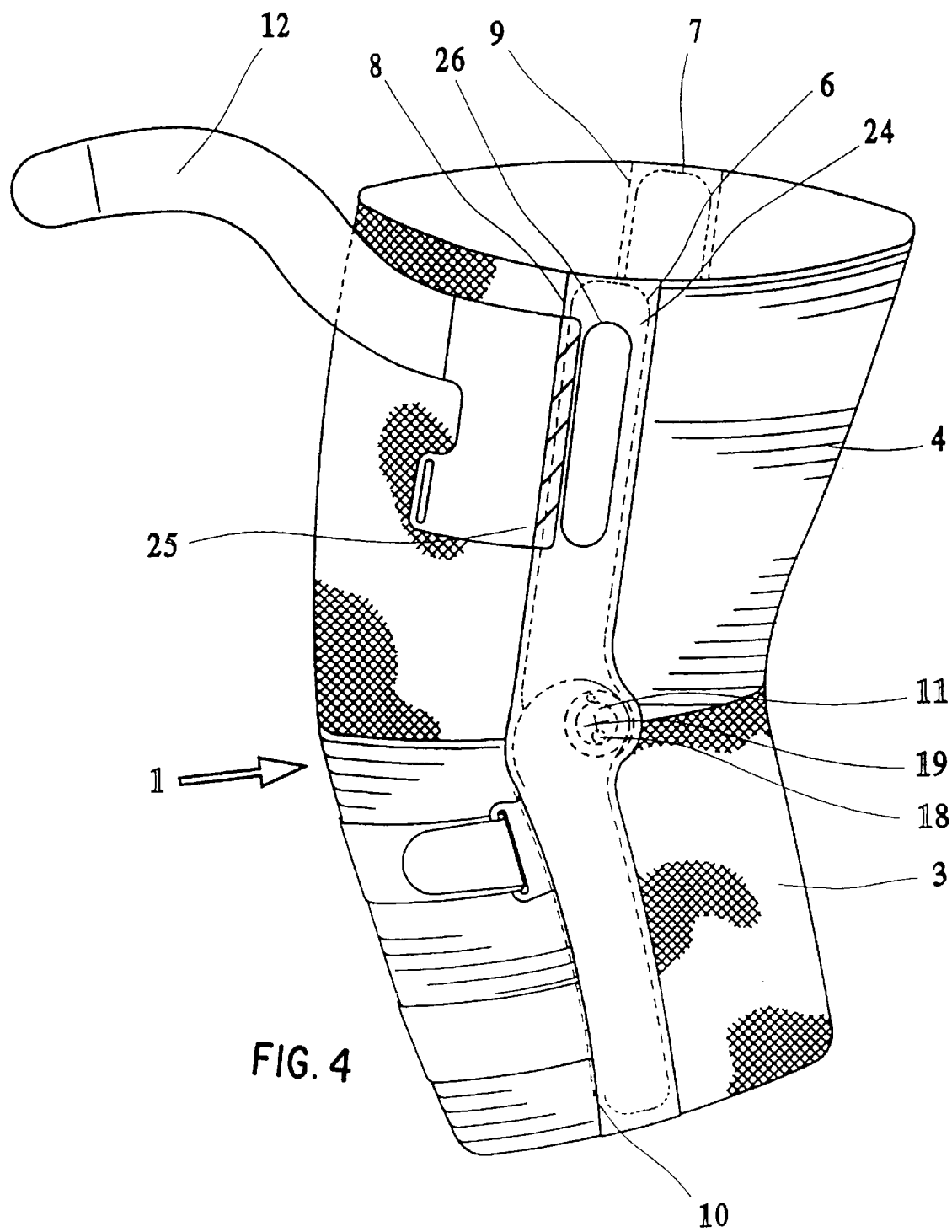
FIG. 4 shows the knee-joint orthesis according to FIG. 1 with a pocket which is to be opened for the insertion and removal of the rail.

FIG. 4 shows the knee-joint orthesis 1 according to FIG. 1, and additionally indicates how the rail 6 (and thus also the rail 7) can be fitted in the orthesis and removed therefrom. The lower part of the rail 6 is fitted into the pocket arranged on the non-elastic tube part 3. The pockets 8, 9 can each be formed as an openable pocket, hereinafter referred to as pocket 24. The pocket 24 is provided for the upper part of the rail 6, and the pocket 10 is provided for the lower part. The pocket 24 has the opening 26 and the covering flap 25 which can be laid across the pocket 24 in the direction toward the elastic tube part 4 and can be fastened to this by means of a hoop-and-loop fastener. In this way, the rail 6 is held securely in the pockets 24 and 10 and cannot slide out from them. When the covering flap 25 is opened, the rail 6 can be removed from the two pockets 24 and 10, for example if this is necessary for cleaning the knee-joint orthesis 1. The same applies to the rail 7 in the pocket 9.

What is claimed is:

1. A knee-joint orthesis with fasteners for fastening the orthesis to the thigh and lower leg of a user, which fasteners are connected to one another via at least one two-part rail comprising a pivot hinge which is offset rearwards in relation to the knee joint during use to adapt to the pattern of movement of the knee-joint, and which includes a pin, wherein the pin is mounted eccentrically in a pivot bearing which connects both two rail parts in a rotationally movable manner and wherein the movement of the knee continuously displaces the position of the pin into a respectively adapted position, and a locking member for fixing the pivot bearing against movement relative to one part of the two-part rail such that the two-parts of the rail are movable about the pin in its adapted position.

2. The knee-joint orthesis as claimed in claim 1, wherein each part of the two-part rail is positioned within a pocket on the fasteners for the thigh and for the lower leg.

3. The knee-joint orthesis as claimed in claim 2, wherein one pocket is open towards the pivot hinge and closed along the rest of its perimeter while the other pocket has an opening extending in its longitudinal direction for the insertion and removal of the rail, and which is covered by a covering flap which can be closed by a hook-and-loop fastener.

* * * * *